US011701181B2

(12) United States Patent
Glassman et al.

(10) Patent No.: US 11,701,181 B2
(45) Date of Patent: Jul. 18, 2023

(54) SYSTEMS, INSTRUMENTS AND METHODS FOR SURGICAL NAVIGATION WITH VERIFICATION FEEDBACK

(71) Applicant: Warsaw Orthopedic, Inc., Warsaw, IN (US)

(72) Inventors: Steven D. Glassman, Louisville, KY (US); Newton H. Metcalf, Jr., Memphis, TN (US); Nicholas Benson, Collierville, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 882 days.

(21) Appl. No.: 16/393,936

(22) Filed: Apr. 24, 2019

(65) Prior Publication Data

US 2020/0337782 A1  Oct. 29, 2020

(51) Int. Cl.
*A61B 34/20* (2016.01)
*A61B 17/17* (2006.01)
(Continued)

(52) U.S. Cl.
CPC .......... *A61B 34/20* (2016.02); *A61B 17/1671* (2013.01); *A61B 17/1703* (2013.01); *A61B 17/1757* (2013.01); *A61B 90/06* (2016.02); *A61B 2017/00026* (2013.01); *A61B 2017/00119* (2013.01); *A61B 2017/320052* (2013.01); *A61B 2034/107* (2016.02); *A61B 2034/2065* (2016.02); *A61B 2034/2072* (2016.02);
(Continued)

(58) Field of Classification Search
CPC ......... A61B 34/10; A61B 34/20; A61B 34/30; A61B 17/16; A61B 17/1659; A61B 17/1671; A61B 17/17; A61B 17/1703; A61B 17/1757
See application file for complete search history.

(56) References Cited

U.S. PATENT DOCUMENTS 7,763,035 B2   7/2010   Melkent et al.
8,634,897 B2   1/2014   Simon et al.
(Continued)

OTHER PUBLICATIONS

StealthStation™ S8 Spinal Navigation Solution, Medtronic PLC Brain Therapies, UC201909309 EN, PMD022116-1.0, © 2019 Medtronic.
(Continued)

*Primary Examiner* — Si Ming Ku
(74) *Attorney, Agent, or Firm* — Fox Rothschild LLP

(57) ABSTRACT

Systems, instruments, and methods for surgical navigation with verification feedback are provided. The systems, instruments, and methods may be used to verify a trajectory of a surgical tool during a procedure. The systems, instruments, and methods may receive one or more captured images of an anatomical portion of a patient; execute a surgical plan to insert the surgical tool into the anatomical portion; receive sensor data collected from one or more sensors being inserted into the anatomical portion; determine whether the sensor data corresponds to the surgical plan; and send, in response to determining that the sensor data does not correspond to the surgical plan, an alert indicating that the surgical tool is not being inserted according to the surgical plan. The one or more sensors may be attached to the surgical tool.

19 Claims, 5 Drawing Sheets

(51) Int. Cl.
  *A61B 90/00* (2016.01)
  *A61B 17/16* (2006.01)
  *A61B 17/00* (2006.01)
  *A61B 34/10* (2016.01)
  *A61B 34/30* (2016.01)
  *A61B 17/32* (2006.01)

(52) U.S. Cl.
  CPC ... *A61B 2034/303* (2016.02); *A61B 2090/065* (2016.02); *A61B 2562/0261* (2013.01); *A61B 2562/18* (2013.01)

(56) References Cited

U.S. PATENT DOCUMENTS

| | | | |
|---|---|---|---|
| 9,066,751 B2 | 6/2015 | Sasso | |
| 10,743,919 B1 | 8/2020 | Williams | |
| 11,000,317 B1 | 5/2021 | Williams | |
| 2005/0273107 A1* | 12/2005 | Stevens | A61B 17/1615 606/916 |
| 2008/0009747 A1* | 1/2008 | Saadat | A61B 18/1492 604/510 |
| 2008/0140180 A1* | 6/2008 | Dolan | A61F 2/954 600/431 |
| 2009/0157059 A1* | 6/2009 | Allen | A61B 34/25 606/1 |
| 2010/0198227 A1* | 8/2010 | Kim | G01B 3/28 606/102 |
| 2011/0015649 A1* | 1/2011 | Anvari | A61B 34/20 606/130 |
| 2014/0276002 A1 | 9/2014 | West et al. | |
| 2016/0074123 A1* | 3/2016 | Bly | A61B 34/20 600/424 |
| 2018/0042514 A1 | 2/2018 | Verard et al. | |

OTHER PUBLICATIONS

The Clinical and Economic Benefits of Using StealthStation® Navigation and O-arm® Imaging Systems for Spine Surgery, Medtronic Surgical Technologies, UC2014181 EN © 2014 Medtronic, Inc. PMD013694-1.0.

International Search Report for PCT/US2019/56904 dated Feb. 4, 2020.

* cited by examiner

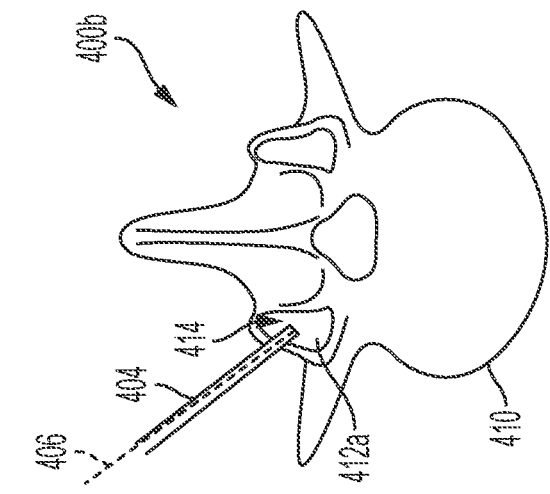
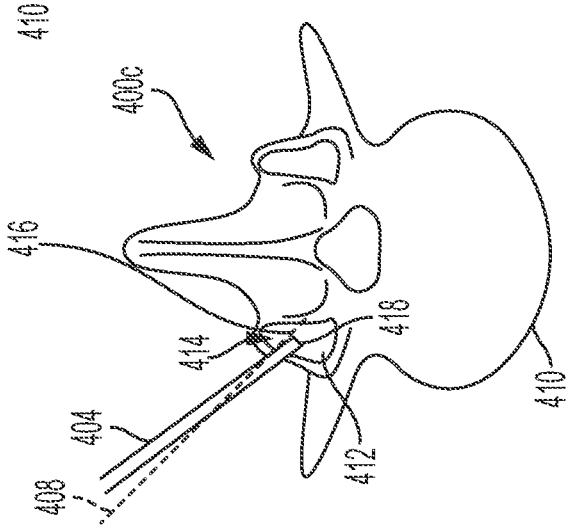
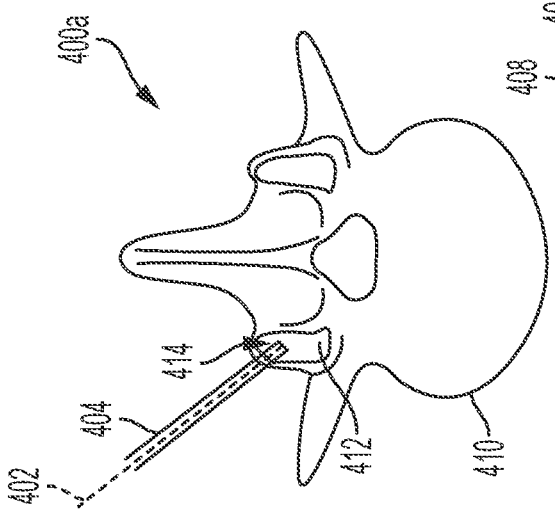
FIG. 4A
FIG. 4B
FIG. 4C

SYSTEMS, INSTRUMENTS AND METHODS FOR SURGICAL NAVIGATION WITH VERIFICATION FEEDBACK

BACKGROUND

Image based surgical techniques have been used to aide physicians in performing a wide variety of delicate surgical procedures. These surgical procedures are used, for example, when a patient' anatomy obscures the visualization of a surgical tool, or when the surgical tool is visible but the patient's anatomy may be difficult to visualize in three dimensions. Such surgical procedures include, for example, spinal implant placement, the alignment of broken bone fragments, and the fixation of bone fractures.

Surgical navigation and robotic systems may use x-ray images or virtual fluoroscopy to visualize the positioning of the surgical tool within the patient's anatomy. By repeatedly acquiring x-ray images during a surgical procedure, real-time placement of the surgical tool relative to the patient's anatomy can be displayed. Additionally, virtual fluoroscopically-based surgical navigation systems may track a trajectory of the surgical tool and superimpose a representation of the surgical tool onto pre-acquired images of the patient's anatomy without requiring x-rays to be repeatedly taken during the surgical procedure.

However, the accuracy of the surgical navigation and robotic systems may be affected by a variety of unaccounted for factors. For example, a patient may re-position his or her body on the surgical table; the surgeon and/or surgical team may inadvertently move the patient; and/or the surgical procedure may cause the patient's anatomy to move, all of which may compromise the accuracy of navigating surgical tools within a patient's anatomy.

SUMMARY

The present disclosure relates generally to image guided medical procedures, and more particularly, to surgical navigation systems, devices, and methods for performing image guided medical procedures.

In one or more embodiments, the disclosed technology relates to a method of verifying a trajectory of a surgical tool during a procedure. In one or more embodiments, the method includes receiving one or more captured images of an anatomical portion of a patient. In one or more embodiments, the method includes executing a surgical plan to insert the surgical tool into the anatomical portion. In one or more embodiments, the method includes receiving sensor data collected from one or more sensors being inserted into the anatomical portion, the one or more sensors being attached to the surgical tool. In one or more embodiments, the method includes determining whether the sensor data corresponds to the surgical plan; and sending, in response to determining that the sensor data does not correspond to the surgical plan, an alert indicating that the surgical tool is not being inserted according to the surgical plan.

In one or more embodiments, the disclosed technology relates to a surgical navigation system for verifying a trajectory of a surgical tool during a procedure. In one or more embodiments, the surgical navigation system includes one or more sensors attached to the surgical tool, an imaging system configured to capture one or more images of an anatomical portion of a patient and to transmit the captured one or more images to a guidance system, and a guidance system configured to operate the surgical tool. In one or more embodiments, the guidance system is configured to receive the one or more captured images. In one or more embodiments, the guidance system is configured to execute a surgical plan to insert the surgical tool, via the robotic arm, into the anatomical portion. In one or more embodiments, the guidance system is configured to receive sensor data collected from the one or more sensors being inserted into the anatomical portion. In one or more embodiments, the guidance system is configured to determine whether the sensor data corresponds to the surgical plan. In one or more embodiments, the guidance system is configured to send, in response to determining that the sensor data does not correspond to the surgical plan, an alert indicating that the surgical tool is not being inserted according to the surgical plan.

In one or more embodiments, the disclosed technology relates to a computer program product including a non-transitory computer-readable storage medium having program instructions embodied therewith for verifying a trajectory of a surgical tool during a procedure, in which the program instructions are executable by one or more processors. In one or more embodiments, the program instructions include receiving one or more captured images of an anatomical portion of a patient. In one or more embodiments, the program instructions include executing a surgical plan to insert the surgical tool into the anatomical portion. In one or more embodiments, the program instructions include receiving sensor data collected from one or more sensors being inserted into the anatomical portion, the one or more sensors being attached to the surgical tool. In one or more embodiments, the program instructions include determining whether the sensor data corresponds to the surgical plan. In one or more embodiments, the program instructions include sending, in response to determining that the sensor data does not correspond to the surgical plan, an alert indicating that the surgical tool is not being inserted according to the surgical plan.

The foregoing and other objects, features and advantages of the invention will be apparent from the following more particular descriptions of exemplary embodiments of the invention as illustrated in the accompanying drawings wherein like reference numbers generally represent like parts of the disclosure.

BRIEF DESCRIPTION OF DRAWINGS

The following drawings are illustrative of particular embodiments of the present disclosure and therefore do not limit the scope of the present disclosure. The drawings are not to scale and are intended for use in conjunction with the explanations in the following detailed description.

FIG. 4A illustrates an example of the surgical navigation procedure.

FIG. 4B illustrates another example of the surgical navigation procedure.

FIG. 4C illustrates another example of the surgical navigation procedure.

DETAILED DESCRIPTION

Figure 1:
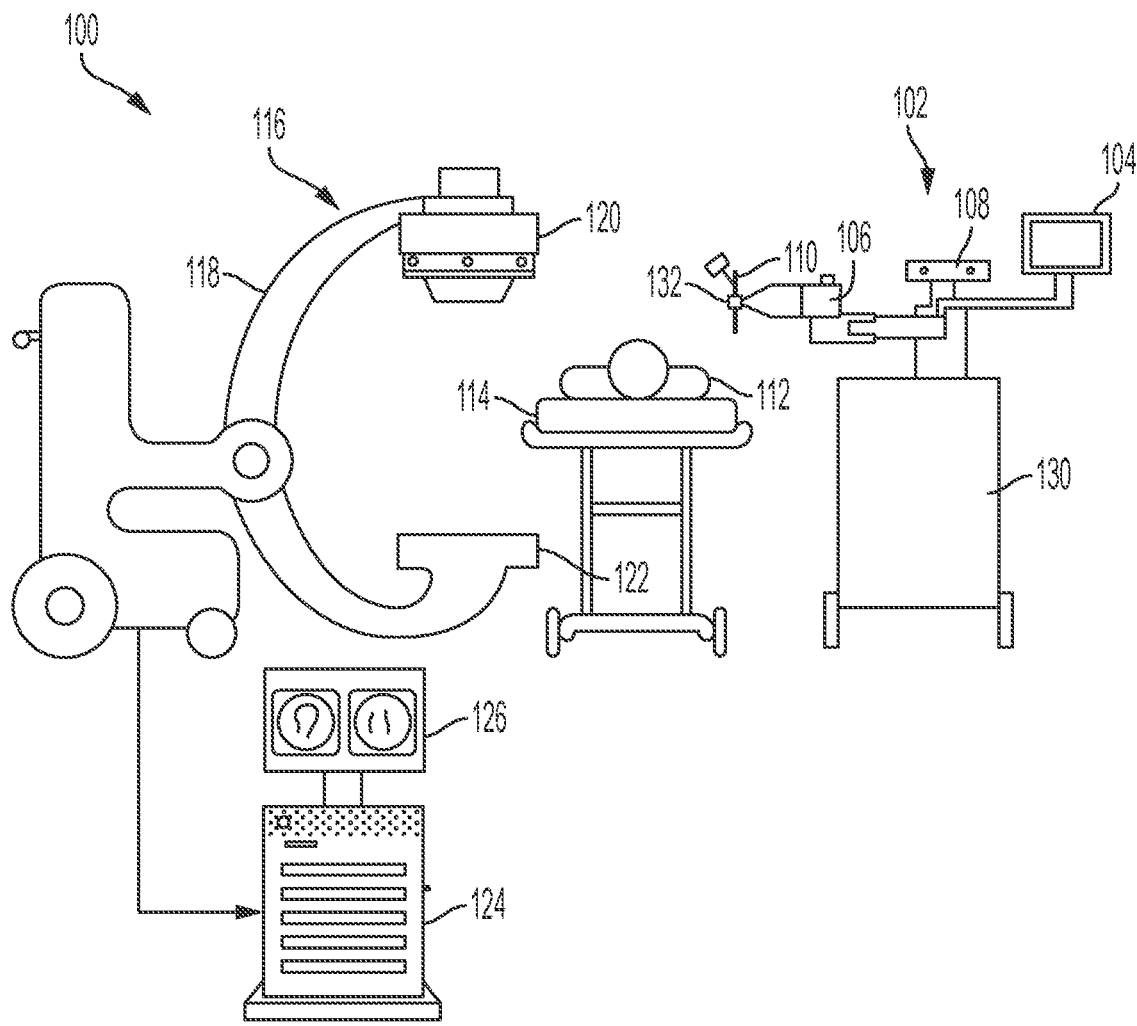
FIG. 1 illustrates a surgical navigation system for spinal surgical procedures, according to one or more embodiments of the present disclosure.

The following discussion omits or only briefly describes certain conventional features related to surgical navigation systems, which are apparent to those skilled in the art. It is noted that various embodiments are described in detail with reference to the drawings, in which like reference numerals represent like parts and assemblies throughout the several views. Reference to various embodiments does not limit the scope of the claims appended hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Embodiments of the present disclosure relate generally, for example, to devices, methods, and systems for image guided medical procedures, and more particularly, to surgical navigation systems, devices, and methods for performing image guided medical procedures, such as, for example, those used in the FluoroNav™ system, which utilizes the StealthStation® Treatment Guidance Platform, both of which are available from Medtronic Sofamor Danek, Inc. The StealthStation® Treatment Guidance Platform, and in particular the StealthStation® Navigation System, is described in part in the "StealthStation™ S8 Spinal Navigation Solution" brochure published by Medtronic, Inc. in 2019 and in "The Clinical and Economic Benefits of Using StealthStation® Navigation and O-Arm® Imaging Systems for Spine Surgery" brochure published by Medtronic, Inc. in 2014. Embodiments of the surgical navigation systems, devices, and methods are described below with reference to FIGS. 1-4C. Embodiments of the surgical navigation systems, devices and methods described herein may be used in combination with robotic systems, such as, for example, the Mazor X™ Stealth Edition, which is available from Medtronic, Inc.

FIG. 1 illustrates an operating environment for spinal surgical procedures, according to one or more embodiments of the present disclosure. FIG. 1 provides only an illustration of one implementation and does not imply any limitations with regard to the environments in which different embodiments may be implemented. Many modifications to the depicted environment may be made by those skilled in the art without departing from the scope of the embodiments herein.

In one or more embodiments, a surgical navigation system, utilized in the operating environment 100 includes a precision guidance system 102 and an imaging system 116. The surgical navigation system enables a surgeon to generate and display images of a trajectory of a surgical instrument within an anatomy of a patient 112 during a surgical procedure. Features of the surgical navigation system are further described in U.S. Pat. No. 8,634,897 B2, the entire disclosure of which is hereby incorporated by reference.

The precision guidance system 102 may include a monitor 104, a robotic arm 106, a camera 108, and a computer including one or more processors and at least one computer readable medium. The computer may be any programmable electronic device or computing system capable of receiving and sending data and performing computer-readable program instructions on the at least one computer readable medium. The computer-readable program instructions may be instructions to operate a surgical navigation procedure illustrated as a method 300 in FIG. 3. The one or more processors may be configured to execute one or more program instructions to verify a trajectory of a surgical tool, such as a pedicle access needle, Jamshidi needle, guidewire, or probe 110, during the surgical navigation procedure. The monitor 104, robotic arm 106, and camera 108 may each be pivotably coupled to the base 130 of the precision guidance system 102. The camera 108 may be an integrated 3D camera with spatial tracking features. The camera 108 may be used to track the movements of the robotic arm 106 in order for the precision guidance system 102 to provide movement instructions to the robotic arm 106.

The monitor 104 may be a control panel for a user to interact with in a sterile area of the operating environment 100. The monitor 104 may display a surgery plan and/or the trajectory of a surgical tool, for example, a probe 110, probe 110a, and/or probe 110b, within an anatomical portion of the patient 112. The monitor 104 may be configured to receive and display images from the imaging system 116.

In order to operate the robotic arm 106, the precision guidance system 102 may provide movement instructions to the robotic arm 106. The precision guidance system 102 may provide the movement instructions in accordance with the surgery plan. The robotic arm 106 may be configured to rotate about one or more axes in order to perform one or more functions of a surgical procedure. The robotic arm 106 may include an instrument holder 132 configured to secure tools, such as surgical tools, to the distal end of the robotic arm 106. The instrument holder 132 may be configured in a variety of shapes to hold a respective tool. For example, the instrument holder 132 may be configured in a shape configured to receive and hold the probe 110, such as probe 110a and/or probe 110b.

The imaging system 116 may include a workstation 124 having a workstation monitor 126, and an image receiving section 120 coupled to an image generating section 122 via an arm 118. The arm 118 is configured in a shape to be positioned above and below the patient 112 laying on the surgical table 114. For example, the arm 118 may be configured in a "C" shape such that the image generating section 122 is positioned at a bottom distal end of the C-shape arm, and the image receiving section 120 is positioned at an upper distal end of the C-shape arm. When the imaging system 118 is positioned to take images of the patient 112, the image generating section 122, the patient 112, and the image receiving section 120 are linearly aligned with one another.

The imaging system 116 may be a computed tomography (CT) fluoroscopic image-based surgical navigation system. The imaging system 116 may acquire and display CT images and/or x-ray images appropriate for a given surgical procedure. However, it should be understood that the imaging system 116 is not confined to use with this particular image guided surgical system. For example, the imaging system 116 may acquire images from other modalities in place of the CT fluoroscopic image-based surgical navigation system. Such modalities may include, by way of non-limiting examples, CT, ultrasound, PET, or magnetic resonance imaging. The CT images and/or x-ray images may be collected when the patient 112 is positioned laying on the surgical table 114 within the arm 118 of the imaging system 116. The images may be preferably taken at a time prior to performing a surgical procedure. The images may be taken from two orthogonal directions, such as anterior-posterior (A-P) and lateral, of the anatomical portion of the patient 112. The imaging system 112 may transmit the acquired images from the image receiving section 120 to the workstation 124, which provides the ability to display the received images via the workstation monitor 126. The imaging system 112 may provide the received images to the precision guidance system 102.

Figure 2A:
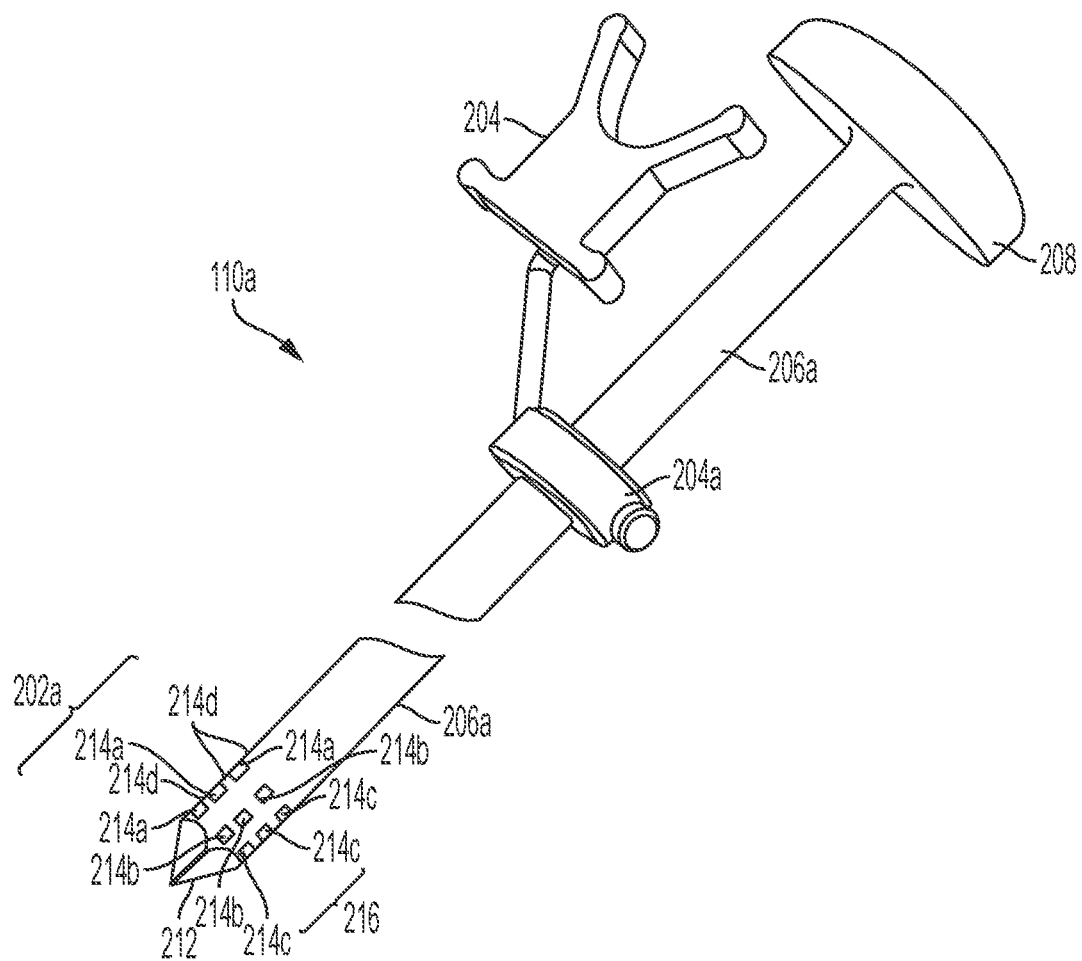
FIG. 2A illustrates a perspective view of a probe, according to one or more embodiments of the present disclosure.

FIG. 2A illustrates a perspective view of the probe 110*a*, according to one or more embodiments of the present disclosure. In one or more embodiments, the probe 110*a* includes a solid body 206*a* having an insertion end 202*a* and an attachment handle 208. The insertion end 202*a* and the handle 208 may be positioned on opposite ends of the solid body 206*a*.

In one or more embodiments, the solid body 206*a* of the probe 110*a* is an elongated rigid structure having a solid center. In one or more cases, the solid body 206*a* is a linear structure. In one or more other cases, at least a portion of the solid body 206*a* is curved. The insertion end 202*a* includes a cutting tip 212 and sensors, such as sensors 214*a*, 214*b*, 214*c*, and 214*d*. In one or more cases, the insertion end 202*a* of the solid body 206*a* may have a linear shape. In one or more other cases, the insertion end 202*a* may have a curved shape. It is noted that FIG. 2A illustrates sensors 214*d* as being located on the rear of the probe 110*a*. The cutting tip 212, similar to a Jamshidi needle, a Pedicle Access Kit (PAK) needle, or the like, may be configured to penetrate through bone and/or tissue. In one or more cases, the cutting tip 212 may include sharp tapered cutting edges, as shown in FIG. 2A. In one or more other cases, the cutting tip 212 may include one or more sharp cutting flutes. In one or more other cases, the cutting tip 212 may be a guide-wire configured to penetrate bone. The insertion end 202*a* may be formed at various diameters and lengths in order to act as a tap for the insertion of a surgical device or implant, such as a pedicle screw.

In one or more embodiments, the sensors 214*a*, 214*b*, 214*c*, and 214*d* may be configured to measure anatomical information, such as bone density and/or tissue density. In one or more embodiments, the sensors 214*a*, 214*b*, 214*c*, and 214*d* may be impedance sensors, pressure sensors, strain gauges, or the like. In one or more cases, the sensors 214*a*, 214*b*, 214*c*, and 214*d* may be of all the same type of sensors. For example, sensors 214*a*, 214*b*, 214*c*, and 214*d* may be all impedance sensors. In one or more other cases, the sensors 214*a*, 214*b*, 214*c*, and 214*d* may be a combination of sensors. For example, one or more of the sensors may be impedance sensors, and one or more other sensors may be pressure sensors.

In one or more embodiments, the solid body 206*a* includes recessed cavities, in which each cavity is configured to house a respective sensor, such that a sensor may be embedded within the probe 110*a*. The recessed cavities may be formed in a shape similar to the shape of a respective sensor, e.g., a recessed cavity may be square-shaped to accommodate a square-shaped sensor. The depth of the recessed cavity may be deep enough to accommodate the thickness of a respective sensor. In one or more cases, when a sensor is positioned within a recessed cavity, the outer surface of the sensor, which does not contact a surface of the recessed cavity, may be flush or substantially flush with the outer surface of the solid body 206*a*.

Figure 2B:
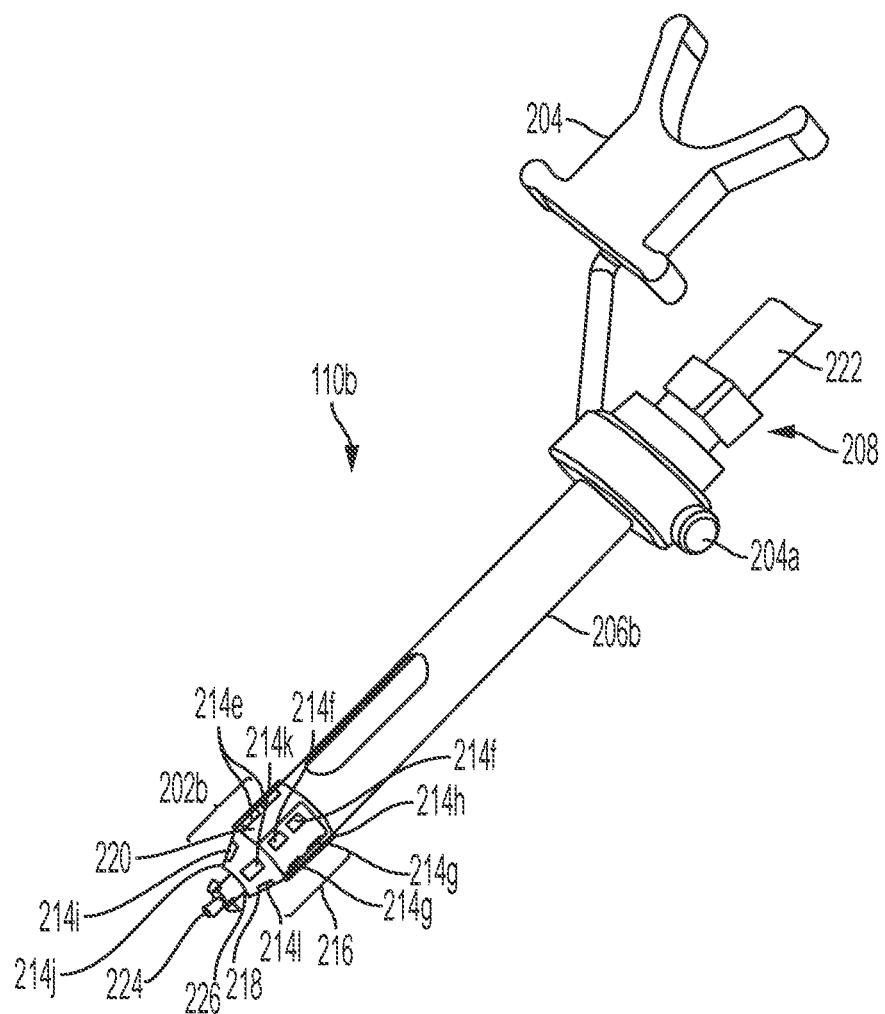
FIG. 2B illustrates a perspective view of a probe, according to one or more embodiments of the present disclosure.

In one or more cases, a protective seal, such as the protective seal 220 shown in FIG. 2B, may cover the sensors and a portion, e.g., the insertion end 202*a*, of the outer surface of the solid body 206*a*. The protective seal may be configured to protect the sensors from being damaged when the probe 110*a* enters an anatomical portion, such as a vertebra, of the patient 112. In one or more cases, when the protective seal is attached to the solid body 206*a*, the outer surface of the protective seal is flush or substantially flush with the outer surface of the proximal portion of the cutting tip 212.

In one or more other embodiments, the solid body 206*a* does not include recessed cavities. The sensors may be positioned on the outer surface of the solid body 206*a*, such that the outer surface of the sensor is raised from the outer surface of the solid body 206*a*. In one or more cases, in order to prevent the sensors from being damaged, the protective seal may cover the sensors positioned on the outer surface of the solid body 206*a*.

The sensors 214*a*, 214*b*, 214*c*, and 214*d* may be arranged circumferentially around the insertion end 202*a*. In one or more embodiments, each set of sensors may be arranged in a sensor array 216. For example, the sensors 214*a* may form a sensor array 216. In one or more cases, the sensor array 216 may be configured as a linear array. In the linear array configuration, each sensor array for sensors 214*a*, 214*b*, 214*c*, and 214*d* may be spaced apart from one another around the insertion end 202*a*, such that the width between each sensor array is equal. In one or more other embodiments, the sensors 214*a*, 214*b*, 214*c*, and 214*d* may be arranged in a spiral shape around the insertion end 202*a*.

In one or more embodiments, the probe 110*a* includes an emitter array 204 attached to the solid body 206*a*, via the clamp 204*a*. The clamp 204*a* may have a cylindrical opening configured to receive the solid body 206*a*. The clamp 204*a* may be fastened to a portion of the solid body 206*a*. The emitter array 204 may be configured to identify the location of the probe 110*a* in three dimensional space relative to a known reference point, such that the probe 110*a* and/or the trajectory of the probe 110*a* may be shown on one or more monitors, such as monitor 104 and workstation monitor 126. The emitter array 204 may transmit sensor data collected by the sensors 214*a*, 214*b*, 214*c*, and 214*d*. The collected sensor data may be information related to the anatomical portion of the patient 112. The emitter array 204 may be configured to receive data from the precision guidance system 102. Features of the emitter array 204 are further described in U.S. Pat. No. 7,763,035 B2, the entire disclosure of which is hereby incorporated by reference.

In one or more embodiments, for the cases in which a portion of the surgical procedure is manually performed by a surgeon, the surgeon can grip the handle 208 and guide the probe 110*a* into an anatomical portion of the patient 112. In one or more other embodiments, the handle 208 may be configured to attach to the instrument holder 132 of the robotic arm 106.

FIG. 2B illustrates a perspective view of the probe 110*b*, according to one or more embodiments of the present disclosure. In one or more embodiments, the probe 110*b* includes a cannulated body 206*b* having an insertion end 202*b* and an attachment handle 208. The insertion end 202*b* and the attachment handle 208 may be positioned on opposite ends of the cannulated body 206b.

In one or more embodiments, the cannulated body 206b of the probe 110b is an elongated rigid structure having a hollow center. The hollow center of the cannulated body 206b is configured to receive a surgical tool. For example, a reamer 222 may be inserted through the hollow center, such that a portion of the reamer head 224 protrudes out of the opening 226 of the insertion end 202b. A bone drill bit, guidewire, needle, dilator, or other instrument may alternatively be inserted in the center of the probe. The opening of the insertion end 202b may be formed at various diameters in order to accommodate surgical tools having different diameters. The surgical tools, such as the reamer 222, an inserter, a distractor, are further described in U.S. Pat. No. 7,763,035 B2, the entire disclosure of which is hereby incorporated by reference.

In one or more cases, the insertion end 202b includes a tapered end 218 that tapers towards the distal end of the probe 110b. The tapered end 218 may be used to facilitate the entry of the probe 110b into the anatomical portion of the patient 112. In one or more other cases, the insertion end 202b is substantially cylindrical and does not include the tapered end 218.

In one or more embodiments, the sensors 214e, 214f, 214g, and 214h include one or more of the same features as sensors 214a, 214b, 214c, and 214d. Accordingly, a description of these features is not repeated. The sensors 214i, 214j, 214k, and 214l include one or more of the same features as sensors 214a, 214b, 214c, and 214d. It is noted that FIG. 2B illustrates sensors 214h and 214j as being located on the rear of the probe 110b. Accordingly, a description of these features is not repeated. Additionally, the sensors 214i, 214j, 214k, and 214l may be positioned on the tapered end 218 of the insertion end 202b. The sensors 214i, 214j, 214k, and 214l may lie on the same angled plane of the tapered end 218. In one or more embodiments, the insertion end 202b of the cannulated body 206b includes recessed cavities having one or more of the same features as the recessed cavities included in the insertion end 202a of the solid body 206a. Accordingly, a description of the recessed cavity features is not repeated.

In one or more embodiments, the probe 110b may include a protective seal 220 covering the sensors and a portion, e.g., the insertion end 202b, of an outer surface of the cannulated body 206b. The protective seal may be configured to protect the sensors from being damaged when the probe 110b enters an anatomical portion, such as a vertebra, of the patient 112. In one or more embodiments, the insertion end 202b may be recessed into the cannulated body 206b a depth equivalent to at or about the thickness of the protective seal 220. When the protective seal 220 is attached to the insertion end 202b, the outer surface of the protective seal 220 may be flush or substantially flush with the outer surface of the cannulated body 206.

In one or more embodiments, the emitter array 204 of the probe 110b includes one or more of the same features as the emitter array 204 of the probe 110a, and the handle 208 of the probe 110b includes one or more of the same features as the handle 208 of the probe 110a. FIG. 2B illustrates the handle 208 being configured to attach to the instrument holder 132 of the robotic arm 106. Accordingly, descriptions of these features are not repeated.

In one or more embodiments, for the cases in which a hole is drilled in a vertebral body and/or a bone screw is inserted therethrough, the drill tip and/or bone screw may include one or more sensors, similar to sensors 214a, 214b, 214c, and 214d. In one or more cases, the one or more sensors may be included in the distal end of the bone screw. Each sensor may be recessed within the bone screw, such that the outer surface of the sensor may be flush or substantially flush with the surface of the recess formed by the thread of the bone screw. In one or more other cases, the one or more sensors may be recessed within the shank of the bone screw. The bone screw may be a cannulated bone screw that includes circuitry and an antenna within the cannulated portion of the head and/or the shank of the bone screw. The circuitry and antenna may be connected to the one or more sensors, in which the circuitry connectors, such as wires, are positioned within the cannulated portion of the bone screw. The circuitry and antenna may be configured to transmit sensor data from the one or more sensors to the precision guidance system 102. The bone screw, having the one or more sensors, may operate with the precision guidance system 102 in a similar manner as the sensors and probe 110a and probe 110b. The bone screw may be, in a non-limiting example, a pedicle screw.

Figure 3:
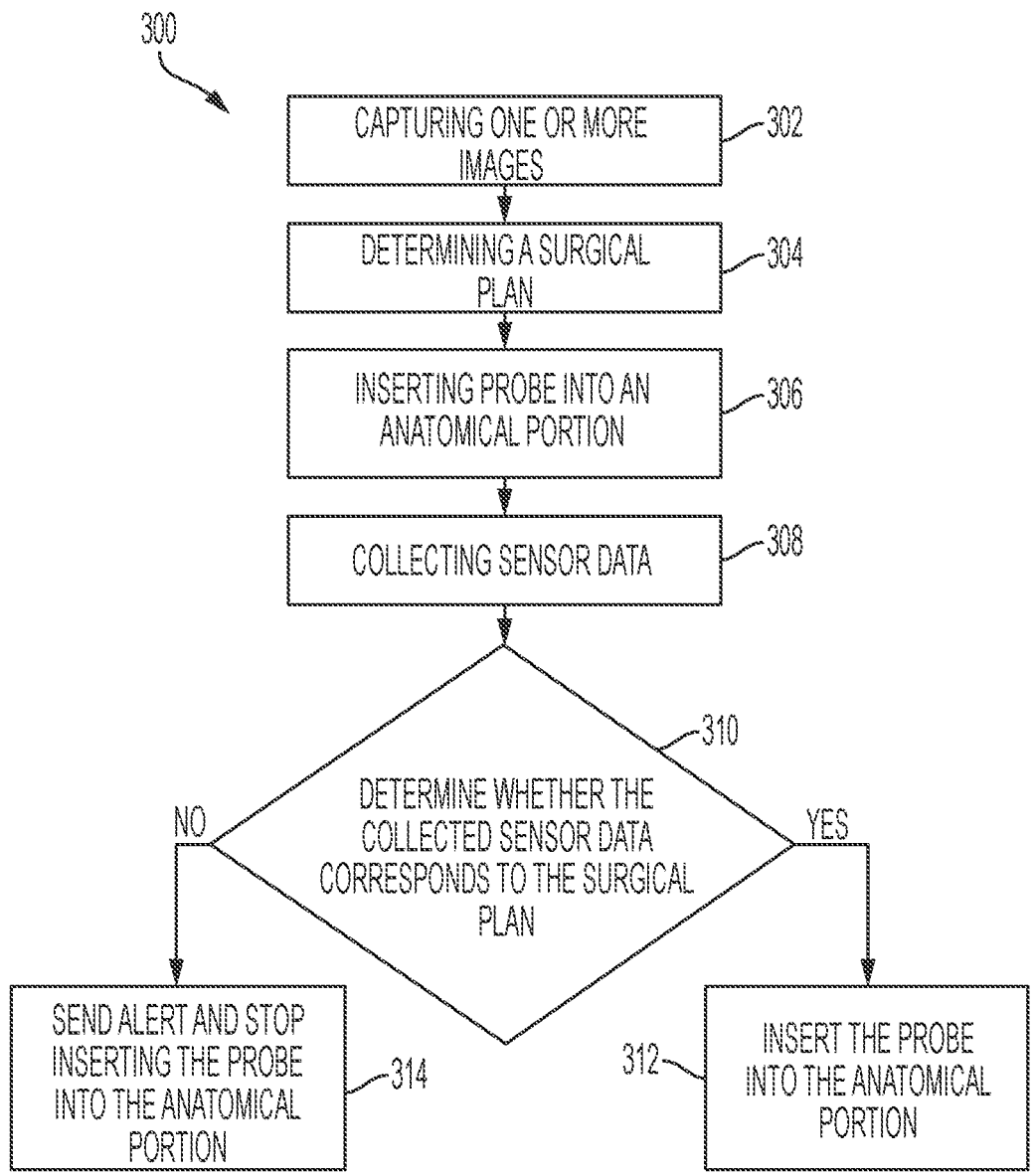
FIG. 3 is a flowchart illustrating a method of a surgical navigation procedure, according to one or more embodiments of the present disclosure.

FIG. 3 is a flowchart illustrating the method 300 of the surgical navigation procedure, according to one or more embodiments of the present disclosure. While the method 300 is described for the sake of convenience and not with an intent of limiting the disclosure as comprising a series and/or a number of steps, it is to be understood that the process does not need to be performed as a series of steps as shown in FIG. 3, but multiple steps can be abstracted into one functional unit that performs both the steps. FIG. 4A illustrates an example 400a of the surgical navigation procedure. FIG. 4B illustrates another example 400b of the surgical navigation procedure. FIG. 4C illustrates another example 400c of the surgical navigation procedure.

In one or more embodiments, one or more images are captured at 302. The one or more images may be preferably captured by the imaging system 116. The one or more captured images may be CT images and/or x-ray images of the anatomical portion of the patient 112 where a surgical procedure will be performed. The CT images, and/or x-ray images may be collected when the patient 112 is positioned laying on the surgical table 114 within the arm 118 of the imaging system 116. In one or more cases, the images may be preferably taken at a time prior to performing the surgical procedure. The images may be taken from two orthogonal directions, such as anterior-posterior (A-P) and lateral, of the anatomical portion, e.g., a portion of vertebra 410, such as a pedicle, of the patient 112. The imaging system 112 may transmit the acquired images from the image receiving section 120 to the workstation 124 and/or the precision guidance system 102.

In one or more embodiments, a surgical plan is determined at 304. In one or more cases, a user, such as a surgeon, may determine the surgical plan to be executed by the precision guidance system 102. Based on the one or more captured images, the surgeon may determine the surgical plan to implant and/or determine a trajectory placement of a surgical device or implant, such as a pedicle screw. The surgical plan may include the path, such as path 404, to implant the surgical device into the anatomical portion of the patient 112. For example, the surgeon may determine that a hole configured to receive a pedicle screw may be formed via path 404, as shown in FIGS. 4A-4C. The surgeon may determine that path 404 enters into a central portion 414 of the left pedicle 412 of a vertebra 410. The surgeon, using the one or more captured images, may determine data related to the anatomical portion, e.g., the bone density of the anatomical portion and/or the bone density around the path 404.

Having determined the surgical plan, the surgical plan may be imported into the workstation 124 and/or the precision guidance system 102. In one or more cases, a mounting platform, such as a fixation bone clamp described in U.S. Pat. No. 9,066,751 and incorporated herein by reference in its entirety, of the precision guidance system 102 may be rigidly attached to the patient at another anatomical portion, such as a spinous process of another vertebra either above or below the target vertebra, of the patient. In one or more other cases, a mounting platform, such as a percutaneous reference pin for use with the precision guidance system 102 may be rigidly attached to the patient at another anatomical portion, such as the posterior superior iliac spine. The precision guidance system 102 may perform a 3D scan of the surgical location, via camera 108 and/or a 3D camera integrated into the robotic arm 106, to reconstruct the 3D volume of the patient 112 and assess the working area for the surgeon. The one or more captured images may be mapped to the 3D scan of the surgical location.

In one or more embodiments, a probe is inserted at 306 into the anatomical location. In one or more embodiments, the robotic arm 106 may begin to insert the probe, e.g. either probe 110a or 110b, into the anatomical portion, e.g., a left pedicle 412 of the vertebra 410 of the patient 112. As the probe is inserted into the anatomical portion, sensor data is collected at 308, preferably by the sensors, such as sensors 214a, 214b, 214c, and 214d of probe 110a or sensors 214e, 214f, 214g, 214h, 214i, 214j, 214k, and 214l of probe 110b. The probe may transmit the collected sensor data to the precision guidance system 102, via the emitter array 204. The precision guidance system 102 may be configured to convert the collected sensor data to Hounsfield units or other measures of bone density and/or tissue density. In one or more embodiments, the probe may transmit the collected sensor data to the precision guidance system 102, and the precision guidance system 102 may convert the collected sensor data in real-time.

Having converted the collected sensor data, a determination is made at 310, preferably by the precision guidance system 102, as to whether the collected sensor data corresponds to the surgical plan. In one or more cases, the precision guidance system 102 may determine whether the collected sensor data corresponds to the surgical plan in periodic time increments. In one or more other cases, the precision guidance system 102 may determine whether the collected sensor data corresponds to the surgical plan continuously while inserting the probe into the anatomical location. In one or more cases, when the surgical plan is created using the one or more captured images, the precision guidance system 102 may determine data related to the anatomical portion. For example, the precision guidance system 102 can determine at least one of the bone density and the tissue density of the anatomical portion and/or at least one of the bone density and the tissue density around the path 404. To determine whether the collected sensor data corresponds to the surgical plan, the precision guidance system 102 may compare the collected sensor data to the data of the anatomical portion determined in the surgical plan. For example, for the cases in which the collected sensor data relates to bone density, the collected sensor data may be compared to the predetermined bone density data of the anatomical portion.

For the cases in which the collected sensor data corresponds to the surgical plan (310:YES), the probe is inserted into the anatomical portion at 312. For example, the precision guidance system 102 determines that the path 402 measured by the sensors corresponds to the path 404 determined by the surgical plan. That is, the bone density data collected by the sensors corresponds to the bone density data predetermined in the surgical plan. In example 400a, the precision guidance system 102 determines that the collected sensor data places the path 402 on an equivalent path or almost equivalent path as the path 404 determined by the surgical plan. That is, the precision guidance system 102 determines that the bone density measured by the sensors while traveling along path 402 corresponds to the predetermined bone density measurements of the vertebral body 410. In another example 400b, the precision guidance system 102 determines that the collected sensor data places the path 402 slightly angled and/or off center from path 404; however, the precision guidance system 102 determines that the collected sensor data is within an acceptable range of the path 404. That is, the bone density of the anatomical portion measured by the sensors may not be equivalent to the predetermined bone density measurements; however, the bone density measured by the sensors may be close enough to the predetermined bone density measurements to be acceptable for the precision guidance system 102. Being within an acceptable range, the robotic arm 106 proceeds to insert the probe into the left pedicle 412 of the vertebra 410.

For the cases in which the collected sensor data does not correspond to the surgical plan (310:NO), an alert is sent and the insertion of the probe into the anatomical location may be stopped at 314. For example, the collected sensor data may not correspond to the surgical plan when the bone density data collected by the sensors is not equivalent to the bone density data predetermined in the surgical plan, and/or the bone density data collected by the sensors may also be outside of the acceptable range of the predetermined bone density data. For the cases in which the collected sensor data does not correspond to the surgical plan, the precision guidance system 102 may send an alert to the surgeon that the collected sensor data does not correspond to the surgical plan, and/or stop the robotic arm 106 from inserting the probe any farther into the anatomical location.

The alert may be provided as an alarm, message, feedback, or other manner. In one or more cases, the alert may also be a graduated visual signal and/or audio signal. For example, for the cases in which the bone density data collected by the sensors deviates from the bone density data predetermined in the surgical plan, a visual signal may appear on the monitor 104 and/or the workstation monitor 126. For instance, if the precision guidance system 102 determines that the bone density data collected by the sensors deviates at or about 1% from the bone density data predetermined in the surgical plan, a yellow warning light may appear on the monitor 104. In another instance, if the precision guidance system 102 determines that the bone density data collected by the sensors deviates at or about 10% from the bone density data predetermined in the surgical plan, an orange warning light may appear on the monitor 104. In yet another instance, if the precision guidance system 102 determines that the bone density data collected by the sensors deviates at or about 20% from the bone density data predetermined in the surgical plan, a red warning light may appear on the monitor 104. In another example, for the cases in which the bone density data collected by the sensors deviates from the bone density data predetermined in the surgical plan, an audio signal may be emitted from the probe 110 and/or the precision guidance system 102. For instance, if the precision guidance system 102 determines that the bone density data collected by the sensors deviates at or about 1% from the bone density data predetermined in the surgical plan, a first audio signal may be emitted as a simple tone from the probe 110 and/or the precision guidance system 102. In another instance, if the precision guidance system 102 determines that the bone density data collected by the sensors deviates at or about 10% from the bone density data predetermined in the surgical plan, a second audio signal may be emitted as a more complex tone than the tone of the first audio signal. In yet another instance, if the precision guidance system 102 determines that the bone density data collected by the sensors deviates at or about 20% from the bone density data predetermined in the surgical plan, third audio signal may be emitted as a more complex tone than the tone of the second audio signal.

In one or more cases, the precision guidance system 102 may automatically stop the robotic arm 106 for the cases in which the collected sensor data does not correspond to the surgical plan. The surgeon may manually stop, redirect or interrupt the automatic or manual insertion upon receiving or perceiving the alert.

In an example implementation 400c, the precision guidance system 102 determines that the collected sensor data places the path 408 outside an acceptable range from path 404. For instance, the path 408 may be at a different insertion angle than path 404, and/or the path 408 may extend beyond the determined end of path 404. That is, the precision guidance system 102 may determine that the bone density measured by the sensors while traveling along path 402 does not corresponds to the predetermined bone density measurements of the vertebral body 410. Determining that the path 408 is outside the acceptable range for path 404, the precision guidance system 102 stops inserting the probe into the left pedicle 412 of the vertebra 410 and sends an alert to the surgeon to indicate that the robotic arm 106 is not following the path 404 of the surgical plan. In one or more cases, the precision guidance system 102 may issue instructions to stop inserting the probe when the insertion angle of the path 408 is determined to be incorrect. In one or more other cases, the precision guidance system 102 may issue instructions to stop inserting the probe when the lead portion 416 of the path 408 extends beyond an end portion 418 of the path 408 determined by the surgical plan.

In one or more embodiments, the precision guidance system 102 may be configured to measure the collected sensor data from each sensor array 216 to determine whether the probe is askew. For example, the precision guidance system 102 may determine whether the values from each of the sensor arrays 216 are equivalent or within an acceptable range from one another. If, for instance, the precision guidance system 102 determines that one of the measurements from a sensor array is not equivalent to the measurements for the other sensor arrays or is not within an acceptable range of measurements, the precision guidance system 102 may determine that the probe is skewed towards the sensor array having the incorrect measurements and/or is approaching an area towards the sensor array having the incorrect measurements in which the probe should not enter.

In one or more embodiments, the data from the sensors may be used to provide an additional source of data to the surgical navigation system 100 to confirm or refute the accuracy of the surgical plan and/or the surgical navigation system 100. The sensor data may act as a feedback loop for the precision guidance system 102 to provide a confidence level and/or accuracy level of the path 402.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques, such as the surgical navigation procedure, may be implemented in hardware, software, firmware, or any combination thereof. If implemented in software, the functions may be stored as one or more computer-readable program instructions or code on a computer-readable medium and executed by a hardware-based processing unit, such as a processor. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

The one or more processors may include one or more digital signal processors (DSPs), general purpose microprocessors, application specific integrated circuits (ASICs), field programmable logic arrays (FPGAs), or other equivalent integrated or discrete logic circuitry. A processor may refer to any of the foregoing structure or any other physical structure suitable for implementation of the described techniques. Also, the techniques could be fully implemented in one or more circuits or logic elements.

The various embodiments described above are provided by way of illustration only and should not be construed to limit the claims attached hereto. Those skilled in the art will readily recognize various modifications and changes that may be made without following the embodiments and applications illustrated and described herein, and without departing from the true spirit and scope of the claims.

What is claimed is:

1. A method of verifying a trajectory of a surgical tool during a procedure, the method comprising:
    receiving one or more captured images of an anatomical portion of a patient;
    executing a surgical plan to insert the surgical tool into the anatomical portion,
        wherein the surgical tool comprises an elongated rigid structure having a hollow center,
        wherein the hollow center is configured to receive a second surgical tool, such that the second surgical tool protrudes out of an insertion end of the surgical tool into the anatomical portion, and
        wherein the surgical tool further comprises one or more impedance sensors attached to the surgical tool and disposed around the insertion end of the surgical tool;
    receiving sensor data collected from the one or more impedance sensors while the second surgical tool is received in the hollow center of the surgical tool and while the second surgical tool is being inserted into the anatomical portion;
    determining whether the sensor data corresponds to the surgical plan; and
    sending, in response to determining that the sensor data does not correspond to the surgical plan, an alert indicating that the surgical tool is not being inserted according to the surgical plan.

2. The method of claim 1, further comprises stopping, in response to determining that the sensor data does not correspond to the surgical plan, the insertion of the surgical tool into the anatomical portion.

3. The method of claim 1, wherein executing the surgical plan comprises determining a path to insert the surgical tool into the anatomical portion.

4. The method of claim 1, wherein executing the surgical plan comprises determining, from the one or more captured images, at least one of bone density and tissue density of the anatomical portion, and
wherein the received sensor data comprises at least one of bone density and tissue density of the anatomical portion.

5. The method of claim 4, wherein determining whether the sensor data corresponds to the surgical plan comprises comparing the at least one of bone density and tissue density of the sensor data to the at least one of bone density and tissue density determined in the surgical plan.

6. The method of claim 5, wherein determining whether the sensor data corresponds to the surgical plan comprises determining whether the at least one of bone density and tissue density of the sensor data is within a range of the at least one of bone density and tissue density determined in the surgical plan.

7. The method of claim 1, further comprises instructing, in response to determining that the sensor data does correspond to the surgical plan, a robotic arm to proceed inserting the surgical tool into the anatomical portion.

8. A surgical navigation system for verifying a trajectory of a surgical tool during a procedure, the surgical navigation system comprising:
the surgical tool comprising an elongated rigid structure having a hollow center,
wherein the hollow center is configured to receive a second surgical tool, such that the second surgical tool protrudes out of an insertion end of the surgical tool into an anatomical portion, and
wherein the surgical tool further comprises one or more impedance sensors attached to the surgical tool and disposed around the insertion end of the surgical tool;
a guidance system; and
an imaging system configured to capture one or more images of the anatomical portion of a patient and to transmit the captured one or more images to the guidance system;
wherein the guidance system is configured to:
receive the one or more captured images,
execute a surgical plan to insert the surgical tool, via a robotic arm configured to operate the surgical tool, into the anatomical portion,
receive sensor data collected from the one or more impedance sensors while the second surgical tool is received in the hollow center of the surgical tool and while the second surgical tool is being inserted into the anatomical portion,
determine whether the sensor data corresponds to the surgical plan, and
send, in response to determining that the sensor data does not correspond to the surgical plan, an alert indicating that the surgical tool is not being inserted according to the surgical plan.

9. The surgical navigation system of claim 8, wherein the second surgical tool is configured to penetrate through at least one of bone and tissue.

10. The surgical navigation system of claim 8, wherein the one or more impedance sensors are attached to the insertion end of the surgical tool, and configured to measure anatomical information of the anatomical portion.

11. The surgical navigation system of claim 10, wherein the one or more impedance sensors are embedded in the insertion end of the surgical tool.

12. The surgical navigation system of claim 10, wherein a protective seal is configured to cover the one or more impedance sensors and a portion of the surgical tool.

13. The surgical navigation system of claim 10, wherein the anatomical information comprises at least one of bone density and tissue density.

14. The surgical navigation system of claim 8, wherein the guidance system is further configured to stop, in response to determining that the sensor data does not correspond to the surgical plan, the insertion of the surgical tool into the anatomical portion.

15. The surgical navigation system of claim 14, wherein the guidance system is further configured to instruct, in response to determining that the sensor data does correspond to the surgical plan, the robotic arm to proceed inserting the surgical tool into the anatomical portion.

16. The surgical navigation system of claim 8,
wherein the guidance system is further configured to determine, from the one or more captured images, at least one of bone density and tissue density of the anatomical portion, and
wherein the received sensor data comprises at least one of bone density and tissue density of the anatomical portion.

17. The surgical navigation system of claim 16, wherein the guidance system is further configured to determine whether the sensor data corresponds to the surgical plan by comparing the at least one of bone density and tissue density of the sensor data to the at least one of bone density and tissue density determined in the surgical plan.

18. The surgical navigation system of claim 17, wherein the guidance system is further configured to determine whether the sensor data corresponds to the surgical plan by determining whether the at least one of bone density and tissue density of the sensor data is within a range of the at least one of bone density and tissue density determined in the surgical plan.

19. A computer program product comprising:
a non-transitory computer-readable storage medium having program instructions embodied therewith for verifying a trajectory of a surgical tool during a procedure, the program instructions executable by one or more processors, the program instructions comprising:
receiving one or more captured images of an anatomical portion of a patient,
wherein the surgical tool comprises an elongated rigid structure having a hollow center,
wherein the hollow center is configured to receive a second surgical tool, such that the second surgical tool protrudes out of an insertion end of the surgical tool into the anatomical portion, and
wherein the surgical tool further comprises one or more impedance sensors attached to the surgical tool and disposed around the insertion end of the surgical tool;
executing a surgical plan to insert the surgical tool into the anatomical portion;
receiving sensor data collected from the one or more impedance sensors while the second surgical tool is received in the hollow center of the surgical tool and while the second surgical tool is being inserted into the anatomical portion;

determining whether the sensor data corresponds to the surgical plan; and sending, in response to determining that the sensor data does not correspond to the surgical plan, an alert indicating that the surgical tool is not being inserted according to the surgical plan.

\* \* \* \* \*